United States Patent
Buice et al.

(10) Patent No.: US 12,383,607 B2
(45) Date of Patent: *Aug. 12, 2025

(54) TOPICAL COMPOSITION FOR IMPROVED HEALING OF OPEN WOUNDS

(71) Applicant: Eleos Pharmaceuticals, Inc., Watkinsville, GA (US)

(72) Inventors: Mona E. Buice, Nicholson, GA (US); David M. Sailors, Athens, GA (US); Joshua Z Greeson, Brooklet, GA (US)

(73) Assignee: Eleos Pharmaceuticals, Inc., Watkinsville, GA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/818,363

(22) Filed: Aug. 28, 2024

(65) Prior Publication Data

US 2025/0025534 A1 Jan. 23, 2025

Related U.S. Application Data

(63) Continuation of application No. 18/056,981, filed on Nov. 18, 2022, now abandoned, which is a
(Continued)

(51) Int. Cl.
*A61K 31/80* (2006.01)
*A61K 9/00* (2006.01)
(Continued)

(52) U.S. Cl.
CPC ............ *A61K 38/28* (2013.01); *A61K 9/0014* (2013.01); *A61K 9/006* (2013.01); *A61K 9/06* (2013.01);
(Continued)

(58) Field of Classification Search
None
See application file for complete search history.

(56) References Cited

U.S. PATENT DOCUMENTS

| 6,155,992 A | 12/2000 | Henning et al. |
| 8,093,211 B2 | 1/2012 | Tennenbaum et al. |

(Continued)

FOREIGN PATENT DOCUMENTS

| CN | 103566359 A | 2/2014 |
| RU | 2203500 C2 | 4/2003 |

(Continued)

OTHER PUBLICATIONS

William, "Diabetes and Wounds: Love the Skin You're in", Voice of the Diabetic, vol. 24, No. 1, Winter 2009, pp. 1-3 (Year: 2009).*

(Continued)

*Primary Examiner* — Kyung S Chang
(74) *Attorney, Agent, or Firm* — Clark & Elbing LLP

(57) ABSTRACT

The present disclosure is concerned with compositions comprising insulin and a pharmaceutically acceptable topical carrier. The present disclosure is also concerned with methods of using these compositions for the treatment of a skin ailment such as a diabetic ulcer. This abstract is intended as a scanning tool for purposes of searching in the particular art and is not intended to be limiting of the present invention.

26 Claims, 5 Drawing Sheets

Related U.S. Application Data continuation of application No. 16/165,502, filed on Oct. 19, 2018, now abandoned.

(60) Provisional application No. 62/678,574, filed on May 31, 2018, provisional application No. 62/574,481, filed on Oct. 19, 2017.

(51) Int. Cl.

| | |
|---|---|
| *A61K 9/06* | (2006.01) |
| *A61K 31/196* | (2006.01) |
| *A61K 31/197* | (2006.01) |
| *A61K 38/28* | (2006.01) |
| *A61K 38/57* | (2006.01) |
| *A61K 47/36* | (2006.01) |
| *A61P 17/02* | (2006.01) |
| *A61P 31/04* | (2006.01) |
| *A61P 41/00* | (2006.01) |
| *A61P 3/10* | (2006.01) |

(52) U.S. Cl.
CPC .............. *A61K 47/36* (2013.01); *A61P 17/02* (2018.01); *A61P 3/10* (2018.01)

(56) References Cited

U.S. PATENT DOCUMENTS

| | | | |
|---|---|---|---|
| 9,993,425 | B2 | 6/2018 | Costantino et al. |
| 11,369,664 | B2 | 6/2022 | Buice et al. |
| 2006/0009373 | A1 | 1/2006 | Martin |
| 2011/0294730 | A1 | 12/2011 | Shantha et al. |
| 2012/0003296 | A1 | 1/2012 | Shantha et al. |
| 2014/0038911 | A1 | 2/2014 | Eickelmann et al. |
| 2015/0094260 | A1 | 4/2015 | Braiman-Wiksman et al. |
| 2015/0150919 | A1* | 6/2015 | Alves Mendes ... A61B 17/3205 604/290 |
| 2015/0250856 | A1 | 9/2015 | Schwarz et al. |
| 2016/0045158 | A1* | 2/2016 | Hsu .................... A61B 5/14532 600/347 |
| 2016/0051683 | A1 | 2/2016 | Banov |
| 2016/0220581 | A1 | 8/2016 | Komorowski et al. |
| 2017/0008945 | A1 | 1/2017 | Madsen et al. |
| 2019/0290736 | A1 | 9/2019 | Buice et al. |
| 2021/0162015 | A1 | 6/2021 | Buice et al. |

FOREIGN PATENT DOCUMENTS

| | | | | |
|---|---|---|---|---|
| WO | WO-2010/097800 | A1 | 9/2010 | |
| WO | WO-2012/135422 | A2 | 10/2012 | |
| WO | WO-2014145484 | A2 * | 9/2014 | ......... A61B 5/14532 |
| WO | WO-2019/079710 | A1 | 4/2019 | |

OTHER PUBLICATIONS

"Novolog (RXList)," dated Jul. 14, 2017, retrieved from <https://web.archive.org/web/20170714054151/https://www.rxlist.com/novolog-drug.htm> (53 pages).
Yazdanpanah et al., "Literature review on the management of diabetic foot ulcer," World J Diabetes. 6(1):37-53 (2015) (18 pages).
Huijberts et al., "Advanced glycation end products and diabetic foot disease," Diabetes Metab Res Rev. 24(S1): S19-S24 (Abstract Only) (Apr. 2008) (3 pages).
Singh et al., "Advanced Glycation End Products and Diabetic Complications," Korean J Physiol Pharmacol. 18: 1-14 (Feb. 2014).
Extended European Seach Report for European Patent Application No. 20759637.0, dated Sep. 30, 2022 (7 pages).
International Search Report and Written Opinion for International Application No. PCT/US2020/018808, mailed May 27, 2020 (15 pages).
Ramarao et al., "Comparative Study between the Effect of Topical Insulin and Normal Saline Dressing in Healing of Diabetic Foot Ulcers," International Journal of Contemporary Medical Research. 4(6): 1337-1339 (Jun. 2017).
Stephen et al., "A Randomized, Controlled Trial to Assess the Effect of Topical Insulin Versus Normal Saline in Pressure Ulcer Healing," Ostomy Wound Manage. 62(6):16-23 (2016) (6 pages).
Liu et al., "Insulin regulates multiple signaling pathways leading to monocyte/macrophage chemotaxis into the wound tissue," Biol Open. 7(1):bio026187 (Jan. 2018) (11 pages).
Oryan et al., "Effects of insulin on wound healing: a review of animal and human evidences," Life Sci. 174:59-67 (Apr. 2017) (9 pages).
Kakanj et al., "Insulin and TOR signal in parallel through FOXO and S6K to promote epithelial wound healing," Nat Commun. 7:12972 (2016) (16 pages).
Azevedo et al., "Effect of Topical Insulin on Second-Degree Burns in Diabetic Rats," Biol Res Nurs. 18(2):181-92 (2015) (12 pages).
Apikoglu-Rabus et al., "Effect of topical insulin on cutaneous wound healing in rats with or without acute diabetes," Clin Exp Dermatol. 35(2):180-5 (2009) (6 pages).
"PCCA MucoloxTM," <https://horstpharmacy.com/wp-content/uploads/2018/05/98891_MucoLoxSpecSheet_PRACT.pdf>, retrieved Jun. 25, 2020 (2010) (3 pages).
Abdelkader et al., "Enhanced cutaneous wound healing in rats following topical delivery of insulin-loaded nanoparticles embedded in poly(vinyl alcohol)-borate hydrogels," Drug Deliv Transl Res. 8(5):1053-1065 (Oct. 2018).
Wang et al., "Effects of topical insulin on wound healing: a review of animal and human evidences," Diabetes Metab Syndr Obes. 13:719-27 (2020) (9 pages).
Nie et al., "Locally administered adipose-derived stem cells accelerate wound healing through differentiation and vasculogenesis," Cell Transplant. 20(2):205-16 (2011).
PCCA Science, Technical Report: Assessment of the Mucoadhesive Properties of MucoloxTM Using a 3D Model of the Human Oral Mucosa. 2015.
Blakytny et al., "The Molecular Biology of Chronic Wounds and Delayed Healing in Diabetes," Diabet Med. 23(6):594-608 (2006).
Barrientos et al., "Clinical application of growth factors and cytokines in wound healing," available in PMC Mar. 30, 2016, published in final edited form as: Wound Repair Regen. 22(5):569-78 (2014) (18 pages).
Sen et al., "Human skin wounds: a major and snowballing threat to public health and the economy," available in PMC Nov. 1, 2010, published in final edited form as: Wound Repair Regen. 17(6):763-71 (2009) (14 pages).
Armstrong et al., "Mind the Gap: Disparity Between Research Funding and Costs of Care for Diabetic Foot Ulcers," Diabetes Care. 36(7):1815-7 (2013).
Hrynyk et al., "Alginate-PEG sponge architecture and role in the design of insulin release dressings," Biomacromolecules. 13(5):1478-85 (2012).
Baquerizo Nole et al., "Wound Research Funding from Alternative Sources of Federal Funds in 2012," Wound Repair Regen. 22(3):295-300 (2014).
Goenka et al., "Role of topical use of insulin in healing of chronic ulcer," Med J Dy Patil Univ 7(5):579-83 (2014) (5 pages).
Boulton et al., "The Global Burden of Diabetic Foot Disease. Lancet," 366(9498):1719-24 (2005).
Zhao et al., "pH and Glucose Dual-Responsive Injectable Hydrogels with Insulin and Fibroblasts as Bioactive Dressings for Diabetic Wound Healing," ACS Appl Mater Interfaces. 9(43):37563-37574 (Nov. 2017).
"MUCOLOXTM (30-4782)," <https://www.pccarx.com/products/PCCAMUCOLOX%E2%84%A2/30-4782/PROPRIETARYBASES>, retrieved on Aug. 2, 2021 (2 pages).
Mekkes et al., "Causes, Investigation and Treatment of Leg Ulceration," Br J Dermtol. 148(3):388-401 (2003).
Ding et al., "Multilayered mucoadhesive hydrogel films based on thiolated hyaluronic acid and polyvinylalcohol for insulin delivery," Acta Biomater. 8(10):3643-51 (2012).
Liao et al., "Hyaluronan: Pharmaceutical Characterization and Drug Delivery," Drug Deliv. 12(6):327-42 (2005).

(56) References Cited

OTHER PUBLICATIONS

Cruz-Cazarim et al., "Prospective insulin-based ophthalmic delivery systems for the treatment of dry eye syndrome and corneal injuries," Eur J Pharm Biopharm. 140:1-10 (2019) (10 pages).
Zhang et al., "Effect of local insulin injection on wound vascularization in patients with diabetic foot ulcer," Exp Ther Med. 11(2):397-402 (2016).
International Search Report and Written Opinion mailed on Dec. 20, 2018 by the International Searching Authority for Patent Application No. PCT/US2018/056697, which was filed on Oct. 19, 2018 and published as WO 2019/079710 on Apr. 25, 2019(Applicant—Mona E. Buice et al.) (10 pages).
Martínez-Jiménez et al., "Effects of Local Use of Insulin on Wound Healing in Non-diabetic Patients," Plast Surg (Oakv). 26(2):75-79 (May 2018).
Liu et al., "Cell and molecular mechanisms of insulin-induced angiogenesis," J Cell Mol Med. 13(11-12):4492-504 (2009).
Lima et al., "Topical insulin accelerates wound healing in diabetes by enhancing the AKT and ERK pathways: a double-blind placebo-controlled clinical trial," PLoS One. 7(5):e36974 (2012) (13 pages).
Blair et al., "Sustained release of insulin from sodium hyaluronate based dry powder formulations after pulmonary delivery to beagle dogs," J Control Release. 91(3):385-394 (2003).
Moura et al., "Recent Advances on the Development of Wound Dressings for Diabetic Foot Ulcer Treatment—A Review," Acta Biomaterialia. 9:7093-14 (2013).
Martínez-Jiménez et al., "Local use of insulin in wounds of diabetic patients: higher temperature, fibrosis, and angiogenesis," Plast Reconstr Surg. 132(6):1015e-1019e (2013) (7 pages).
Pakyari et al., "Critical Role of Transforming Growth Factor Beta in Different Phases of Wound Healing," Adv Wound Care (New Rochelle). 2(5):215-224 (2013).
Zagon et al., "Use of topical insulin to normalize corneal epithelial healing in diabetes mellitus," Arch Ophthalmol. 125(8):1082-8 (2007).
Rafehi et al., "Genetic and Epigenetic Events in Diabetic Wound Healing," Int Wound J. 8(1):12-21 (2011).
Negrini et al., "Effects of topical insulin on second-intention wound healing in the red-eared slider turtle (*Trachemys scripta* elegans)—a controlled study," BMC Vet Res. 13(1):160 (Jun. 2017) (10 pages).
Su et al., "Chemokine Regulation of Neutrophil Infiltration of Skin Wounds," Adv Wound Care (New Rochelle). 4(11):631-640 (2015).
Sreenivas et al., "Thiolated Chitosans: Novel Polymers for Lucoadhesive Drug Delivery—A Review," Trop J Pharm Res. 7(3):1077-88 (2008).
Armstrong et al., "Diabetic Foot Ulcers and Vascular Insufficiency: Our Population Has Changed, but Out Methods Have Not," J Diabetes Sci Technol. 5(6):1591-5 (2011).
Loots et al., "Differences in Cellular Infiltrate and Extracellular Matrix of Chronic Diabetic and Venous Ulcers Versus Acute Wounds," J Invest Dermatol. 111 (5):850-7 (1998).
Preedy et al., "Novel coatings in biotechnology trends in inhaler devices," Inhaler Devices: Fundamentals, Design and Drug Delivery, Woodhead Publishing Limited, 37-50 (2013).
Dawoud et al., "Insulin mucoadhesive liposomal gel for wound healing: a formulation with sustained release and extended stability using quality by design approach," AAPS PharmSciTech. 20(4):158 (2019) (15 pages).
Yu et al., "Topical insulin accelerates cutaneous wound healing in insulin-resistant diabetic rats," Am J Transl Res. 9(10):4682-4693.
Extended European Search Report for European Patent Application No. 18868249.6, mailed Jun. 21, 2021 (8 pages).
Vatankhah et al., "Effect of systemic insulin treatment on diabetic wound healing," available in PMC Apr. 1, 2018, published in final edited form as: Wound Repair Regen. 25(2):288-291 (Apr. 2017) (9 pages).
Rayment et al., "Increased Matrix Metalloproteinase-9 (MMP-9) Activity Observed in Chorinc Wound Fluid is Related to the Clinical Severity of the Ulcer," Br J Dermatol. 158(5):951-61 (2008).
Cole-King et al., "Psychological Factors and Delayed Healing in Chronic Wounds," Psychosom Med. 63(2):216-20 (2001).
Liu et al., "Increased Matrix Metalloproteinase-9 Predicts Poor Wound Healing in Diabetic Foot Ulcers," Diabetes Care. 32(2):117-9 (2009).

\* cited by examiner

TOPICAL COMPOSITION FOR IMPROVED HEALING OF OPEN WOUNDS

CROSS-REFERENCE TO RELATED APPLICATIONS

This Application claims the benefit of U.S. Provisional Application No. 62/574,481, filed on Oct. 19, 2017, and U.S. Provisional Application No. 62/678,574, filed on May 31, 2018, the contents of which are incorporated herein by reference in their entireties.

BACKGROUND

Skin ulcerations such as diabetic ulcers have a significant impact on societies in both developed and developing countries around the world (Boulton et al. (2005) *Lancet.* 366: 1719). For example, in the United Kingdom (UK), they affect an estimated 1% of the total UK adult population, and as high as 5% of the UK population over 65 (Mekkes et al. (2003) *Br. J. Dermatol.* 148: 388-401). These devastating wounds have an enormous negative impact on an individual's quality of life—leading to loss of mobility and sleep deprivation and contributing to increased risk of amputation, anxiety, and depression (Kerr M. Foot Care for People with Diabetes: The Economic Case for Change. *NHS Diabetes Rep.* 2012; Baquerizo Nole et al. (2014) *Wound Repair Regen.* 22: 295-300; Jones et al. (2008) *Nurs. Stand.* 22: 53-61; Cole-King and Harding (2001) *Psychosom Med.* 63: 216-220; Armstrong et al. (2013) *Diabetes Care* 36: 1815-1817). With respect to diabetic foot ulcers (DFU) specifically, diabetic individuals possess a 23-fold increase in the rate of amputation following ulceration compared with non-diabetics, with up to 85% of amputations preceded by DFUs (Armstrong et al. (2013) *Diabetes Care* 36: 1815-1817). Moreover, the 5-year mortality rates associated with DFUs or DFU-related amputations have been found to be as high as or higher than those of breast and prostate cancer (Armstrong et al. (2011) *J. Diabetes Sci. Technol.* 5: 1591-1595). With an increasing frequency of diabetes and obesity, along with an ageing population, these values are only expected to rise.

Despite the large impact of these wounds, there are surprisingly limited options available for treating them. While conventional strategies such as debridement, negative pressure therapy, and offloading orthotics can lead to successful wound closure in some patients (Alavi et al. (2014) *J. Am. Acad. Dermatol.* 70: 21.e1-24), these treatments are ineffective for many others. Often this resistance stems from underlying biological changes that affect the ability of cells within the skin to properly carry out the process of tissue repair. See, e.g., Blakytny and Jude (2006) *Diabet. Med.* 23: 594-608; Loots et al. (2002) *Eur. J. Cell Biol.* 81: 153-160; Loots (1999) *Arch. Dermatol. Res.* 291: 93-99; Loots (1998) *J. Invest. Dermatol.* 111: 850-857; Rayment et al. (2008) *Br. J. Dermatol.* 158: 951-961; Liu et al. (2009) *Diabetes Care.* 32: 117-119; Rafehi et al. (2011) *Int. Wound J.* 8: 12-21). Thus, there remains a need for compositions capable of treating skin ailments such as diabetic ulcers and methods of making and using same.

SUMMARY

In accordance with the purpose(s) of the invention, as embodied and broadly described herein, the invention, in one aspect, relates to compositions and methods for use in the treatment of skin ailments such as, for example, burns, sores, lacerations, blisters, insect bites, surgical incisions, and ulcers (e.g., diabetic ulcers).

Disclosed are topical compositions comprising insulin and a pharmaceutically acceptable topical carrier.

Also disclosed are topical compositions comprising: (a) a mucoadhesive polymer carrier comprising at least two polysaccharide polymers; and (b) insulin.

Also disclosed are methods for treating a skin ailment in a subject, the method comprising the step of topically administering to the skin ailment an effective amount of a disclosed topical composition.

Also disclosed are methods for making a disclosed topical composition, the method comprising the step of combining a mucoadhesive polymer carrier and insulin, wherein the mucoadhesive polymer carrier comprises at least two polysaccharide polymers.

Also disclosed are kits comprising a disclosed topical composition and one or more of: (a) an agent known to treat a skin ailment; and (b) instructions for treating a skin ailment.

Also disclosed are methods for treating a skin ailment having an outer edge in a subject, the method comprising the steps of: (a) obtaining a biological sample from the skin ailment or from a surrounding tissue, wherein the surrounding tissue is within about one inch of the outer edge: (b) measuring the subject's blood sugar levels in the biological sample; and (c) managing the wound via administration of an antibiotic, debridement, off-loading, revascularization, hyperbaric oxygen therapy, administration of a wound care product, negative-pressure wound therapy, or a combination thereof.

Also disclosed are methods for treating a skin ailment having an outer edge in a subject, the method comprising managing the wound via administration of an antibiotic, debridement, off-loading, revascularization, hyperbaric oxygen therapy, administration of a wound care product, negative-pressure wound therapy, or a combination thereof, wherein the subject was previously identified as being in need of treatment of the skin ailment by the steps of: (a) obtaining a biological sample from the skin ailment or from a surrounding tissue, wherein the surrounding tissue is within about one inch of the outer edge; and (b) measuring the subject's blood sugar levels in the biological sample.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The features, nature, and advantages of the present disclosure will become more apparent from the detailed description set forth below when taken in conjunction with the drawings, in which like reference characters are used to identify like elements correspondingly throughout the specification and drawings.

Figure 1:
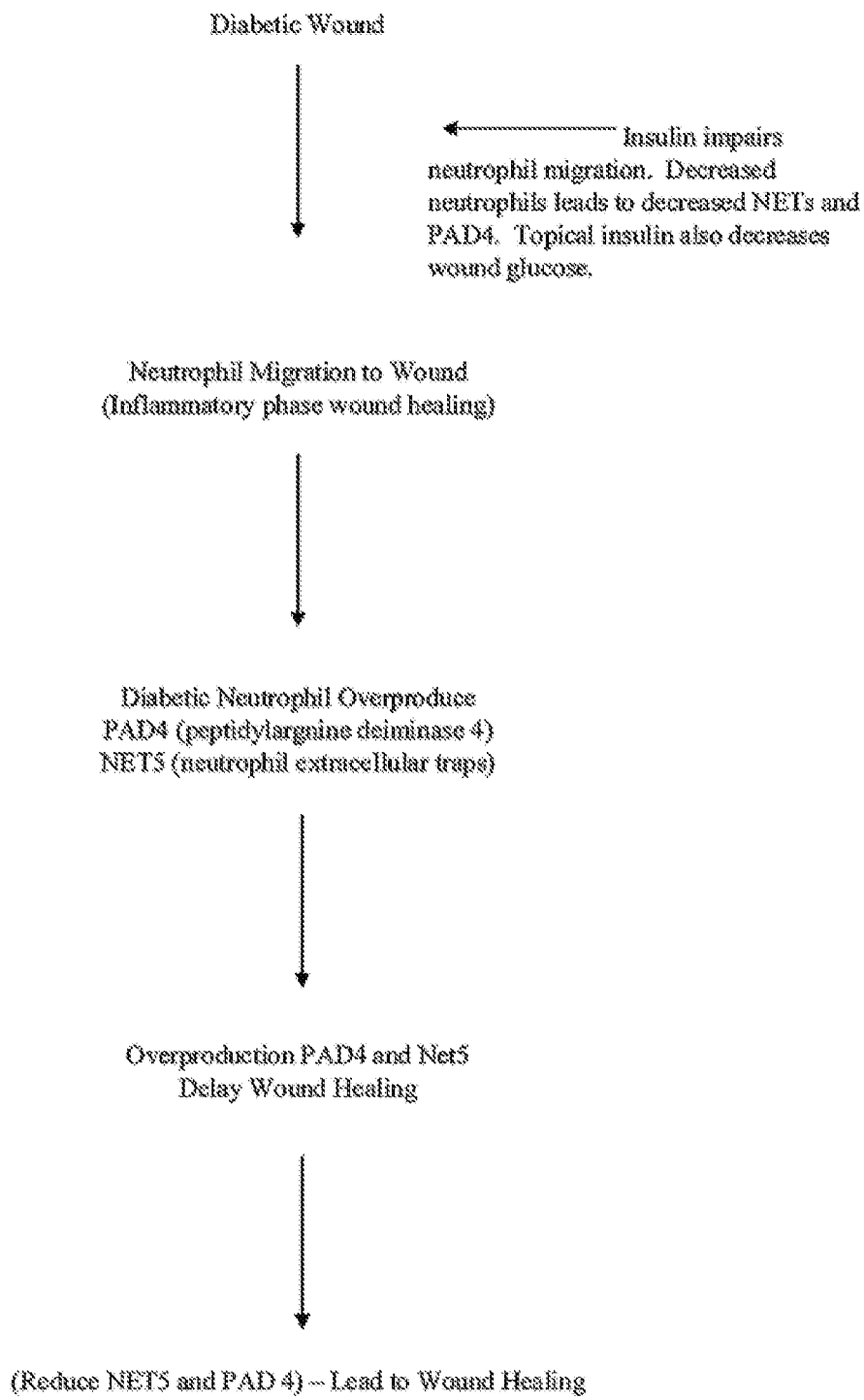
FIG. 1 shows a representative flow chart illustrating a proposed mechanism of diabetic wound healing.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present invention is not entitled to antedate such publication by virtue of prior invention. Further, the dates of publication provided herein may be different from the actual publication dates, which can require independent confirmation.

A. Definitions

As used in the specification and the appended claims, the singular forms "a," "an" and "the" include plural referents unless the context clearly dictates otherwise. Thus, for example, reference to "a mucoadhesive polymer" or "a skin ailment" includes mixtures of two or more such mucoadhesive polymers or skin ailments, and the like.

As used in the specification and in the claims, the term "comprising" can include the aspects "consisting of" and "consisting essentially of."

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the term "pharmaceutically acceptable topical carrier" refers to a material, composition, diluent, or vehicle that is suitable for application to skin or mucosal surfaces, without undue toxicity, irritation, or allergic response. Examples of pharmaceutically acceptable topical carriers include, but are not limited to, creams, lotions, ointments, pastes, jellies, and gels. In various aspects, the pharmaceutically acceptable topical carrier is known as being useful in cosmetic agents and toiletry agents such as, for example, sunscreen and other sun products, anti-aging agents, moisturizing agents, and baby creams.

As used herein, the term "mucoadhesive polymer" refers to a polymer having a good in vivo mucosal absorption rate, safety, and degradability. The mucoadhesive polymer used in the present invention may be synthesized or may be naturally-occurring materials. Examples of naturally-occurring mucoadhesive polymers include, but are not limited to, chitosan, hyaluronate, alginate, gelatin, collagen, and derivatives thereof. Examples of synthetic mucoadhesive polymers include, but are not limited to, poly(acrylic acid), poly(methacrylic acid), poly(-lysine), poly(ethylene imine), poly(2-hydroxy ethyl methacrylate), and derivatives or copolymers thereof.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with an ailment, disease, or disorder. The term "patient" includes human and veterinary subjects.

As used herein, the term "treatment" refers to the medical management of a patient with the intent to cure, ameliorate, stabilize, or prevent an ailment, disease, pathological condition, or disorder. This term includes active treatment, that is, treatment directed specifically toward the improvement of a skin ailment, disease, pathological condition, or disorder, and also includes causal treatment, that is, treatment directed toward removal of the cause of the associated skin ailment, disease, pathological condition, or disorder. In addition, this term includes palliative treatment, that is, treatment designed for the relief of symptoms rather than the curing of the skin ailment, disease, pathological condition, or disorder; preventative treatment, that is, treatment directed to minimizing or partially or completely inhibiting the development of the associated skin ailment, disease, pathological condition, or disorder; and supportive treatment, that is, treatment employed to supplement another specific therapy directed toward the improvement of the associated skin ailment, disease, pathological condition, or disorder. In various aspects, the term covers any treatment of a subject, including a mammal (e.g., a human), and includes: (i) preventing the skin ailment from occurring in a subject that can be predisposed to the skin ailment but has not yet been diagnosed as having it; (ii) inhibiting the skin ailment, i.e., arresting its development; or (iii) relieving the skin ailment, i.e., causing regression of the skin ailment. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compositions or methods disclosed herein.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "dosage form" means a pharmacologically active material in a medium, carrier, vehicle, or device suitable for administration to a subject. A dosage forms can comprise inventive a disclosed composition or a product of a disclosed method of making, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed composition or a product of a disclosed method of making, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-HIV agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors: immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

The term "pharmaceutically acceptable" describes a material that is not biologically or otherwise undesirable, i.e., without causing an unacceptable level of undesirable biological effects or interacting in a deleterious manner.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

B. Topical Compositions

In one aspect, disclosed are topical compositions comprising insulin and a pharmaceutically acceptable topical carrier. The pharmaceutically acceptable carrier can, for example, be any known carrier suitable for topical applications. According to some aspects, the pharmaceutically acceptable carrier is not a cyanoacrylate polymer carrier.

In one aspect, disclosed are topical compositions comprising: (a) a mucoadhesive polymer carrier comprising at least two polysaccharide polymers; and (b) insulin.

In a further aspect, the pharmaceutically acceptable topical carrier is a mucoadhesive polymer carrier. In a still further aspect, the mucoadhesive polymer carrier comprises at least two polysaccharide polymers. In yet a further aspect, the composition consists essentially of the mucoadhesive polymer carrier and insulin. Mucoadhesion is commonly defined as the adhesion between two materials, at least one of which is a mucosal surface. Over the past few decades, mucosal drug delivery has received a great deal of attention. Mucoadhesive dosage forms may be designed to enable prolonged retention at the site of application, providing a controlled rate of drug release for improved therapeutic outcome. Application of dosage forms to mucosal surfaces may be of benefit to drug molecules not amenable to the oral route, such as those that undergo acid degradation or extensive first-pass metabolism. The mucoadhesive ability of a dosage form is dependent upon a variety of factors, including the nature of the mucosal tissue and the physicochemical properties of the polymeric formulation.

Mucoadhesion has recently shown renewed interest for prolonging the residence time of mucoadhesive dosage forms through various mucosal routes in drug delivery application. For example, mucoadhesive-based topical and local systems have shown enhanced bioavailability. Mucoadhesive drug delivery gives rapid absorption and good bioavailability due to its considerable surface area and high blood flow. Drug delivery across the mucosa bypasses the first-pass hepatic metabolism and avoids the degradation of gastrointestinal enzymes. Thus, mucosal drug delivery systems could be of value in delivering a growing number of pharmaceutical agents.

In a further aspect, the pharmaceutically acceptable topical carrier is zinc oxide topical cream. Zinc oxide topical cream is commonly used to treat and prevent diaper rash, as well as to protect skin from being irritated and wet due to diaper use. Examples of zinc oxide topical creams include, but are not limited to, Ammens Medicated, Balmex, Boudreauxs Butt Paste, Critic-Aid Skin Care Pack, Delazinc, Desitin, Hemorrodil, Lassars Paste, Medi-Paste, Periguard, Perishield, and Prevacare Personal Protective.

In various aspects, topical compositions of the present invention can be in any form suitable for topical use such as, for example, an aerosol, cream, ointment, lotion, dusting powder, gel, jelly, and the like. These formulations can be prepared via conventional processing methods known to one skilled in the art. Thus, in various aspects, the pharmaceutically acceptable carrier is selected from a cream, a lotion, a gel, a foam, an emulsion, a mucoadhesive polymer carrier, a spray, normal saline, dextrose 5% in water (D5W), lactated ringers solution, and sterile water.

In a further aspect, the topical composition is an ointment, a gel, a jelly, an oil, a cream, a paste, an aerosol foam, an aerosol spray, a lotion, or a powder. In a still further aspect, the topical composition is a gel.

In a further aspect, an effective amount is a therapeutically effective amount. In a still further aspect, an effective amount is a prophylactically effective amount.

In a further aspect, the topical composition is administered to a mammal. In a still further aspect, the mammal is a human. In an even further aspect, the human is a patient.

In a further aspect, the topical composition is used to treat a skin ailment such as, for example, a burn, a sore, a laceration, a blister, an insect bite, a surgical incision, and an ulcer. In a still further aspect, the topical composition is used to treat a diabetic ulcer.

In a further aspect, the composition further comprises an additive. Examples of additives include, but are not limited to, diluents, buffers, binders, surface-active agents, lubricants, humectants, pH adjusting agents, preservatives (including anti-oxidants), emulsifiers, occlusive agents, opacifiers, antioxidants, colorants, flavoring agents, gelling agents, thickening agents, stabilizers, and surfactants, among others.

In a further aspect, the composition further comprises one or more of an anti-infective agent, an anti-inflammatory agent, a neuropathic pain agent, and a vasodilating agent.

It is understood that the disclosed compositions can be employed in the disclosed methods of using.

1. Mucoadhesive Polymer Carriers

In one aspect, the disclosed compositions comprise a mucoadhesive polymer carrier comprising at least two polysaccharide polymers. Examples of polysaccharide polymers include, but are not limited to, amylopectin, pullulan, sodium hyaluronate, and tamarind xyloglucan. In a further aspect, the mucoadhesive polymer carrier comprises pullulan, sodium hyaluronate, tamarind xyloglucan, and *Zea mays* starch.

The adhesion of polymeric material to the mucosal tissue is referred to as mucoadhesion (Andrews et al. (2009) *Eur. J. Pharm. Biopharm.* 71 (3): 505-518). The attachment of a mucoadhesive polymer to the body tissue increases the residence time of the drug into the body and likely improves patient compliance. The mucoadhesive polymer remains in contact with the mucin or tissue layer either until it dissolves or until the mucous membrane replaces itself, as in the case of cross-linked polymers (Leung and Joseph. Water soluble polymer bioadhesive drug delivery. ACS Symp. Series. 1991; Vol. 467, 350-366). This concept was originally utilized to prolong the residence time of the ocular drug delivery system; however, a number of attempts have been made to utilize this concept to perform various targeted drug deliveries such as, for example, buccal, oral, nasal, ocular, and vaginal drug delivery (Sreenivas and Pai (2008) *Trop. J. Pharm. Res.* 7 (3): 1077-1088. Bioadhesives are designed in various dosage forms including, but not limited to, sprays, pumps, lozenges, tablets, gels, chewing gums, and patches. Mucoadhesive polymers are gaining interest day by day due to their site specificity, increased residence time, improved bioavailability, prevention of first pass metabolism, and enzyme degradation (Andrews et al. (2009) *Eur. J. Pharm. Biopharm.* 71 (3): 505-518). In various aspects, a mucoadhesive polymer is hydrophilic, a non-irritant, has good wetting properties, is compatible with the excipient, does not degrade on storage during its shelf life, is inexpensive, and is easily cleared from the body. Hence, without wishing to be bound by theory, the success of this delivery system likely depends on the proper knowledge and mechanism of interaction of bioadhesive polymers to the mucin and body tissue, the anatomy of the mucous membrane, and the composition of mucous.

In a further aspect, the mucoadhesive polymer carrier comprises at least two polysaccharide polymers. Examples of polysaccharide polymers include, but are not limited to, chitosan, methyl cellulose, hyaluronic acid, hydroxy propyl methylcellulose, hydroxyl propyl cellulose. Xanthan gum, gellan gum, guar gum, and Carrageenan. Cellulose and its derivatives have been reported to have surface active properties in addition to its film-forming capability. Cationic cellulose derivatives (e.g., cationic hydroxyethyl celluloses) have been used in conjunction with various anionic polymers for the development of sustained delivery systems.

In a further aspect, the mucoadhesive polymer carrier comprises a synthetic mucoadhesive polymer. Examples of synthetic mucoadhesive polymers include, but are not limited to, cellulose derivatives, poly(acrylic acid) polymers, poly(hydroxyethyl methylacrylate), poly(ethylene oxide), poly(vinyl pyrrolidone), and poly(vinyl alcohol).

In a further aspect, the mucoadhesive polymer carrier comprises a natural mucoadhesive polymer. Examples of natural mucoadhesive polymers include, but are not limited to, tragacanth, sodium alginate, karaya gum, guar gum, xanthan gum, soluble starch, gelatin, pectin, and chitosan.

In a further aspect, the mucoadhesive polymer carrier comprises a hydrophilic polymer (i.e., the polymer is soluble in water). Matrices developed with these polymers swell when put into an aqueous media with subsequent dissolution of the matrix. The polyelectrolytes extend greater mucoadhesive property. Examples of hydrophilic polymers include, but are not limited to, poloxamer, hydroxypropyl methyl cellulose, methyl cellulose, poly(vinyl alcohol), and poly(vinyl pyrrolidone).

In a further aspect, the mucoadhesive polymer carrier comprises a hydrogel. Hydrogels can be defined as three-dimensionally crosslinked polymer chains which have the ability to hold water within its porous structure. The water holding capacity of the hydrogels is mainly due to the presence of hydrophilic functional groups like hydroxyl, amino and carboxyl groups. In addition to the drug targeting, mucoadhesive hydrogel based formulations are also used to improve the bioavailability of a poorly water soluble drug.

In various aspects, mucoadhesive polymer carriers provide improved release of and improved adhesion time of the insulin transiting through the skin. Thus, without wishing to be bound by theory, in a further aspect, once a topical composition that includes a mucoadhesive polymer carrier is attached to the walls of the skin tissue, the polymeric emulsifiers within the mucoadhesive polymer carrier break down and release the insulin. In a still further aspect, insulin is released at a desired rate during a desired period of time.

In a further aspect, the mucoadhesive polymer carrier is an ointment, a gel, a jelly, an oil, a cream, a paste, an aerosol foam, an aerosol spray, a lotion, or a powder. In a still further aspect, the mucoadhesive polymer carrier is a gel.

In a further aspect, the mucoadhesive polymer carrier further comprises one or more of isomalt, glycerin, poloxamer 407, simethicone, carbomers, sodium benzoate, potassium sorbate, and disodium EDTA. In a still further aspect, the mucoadhesive polymer carrier further comprises isomalt, glycerin, poloxamer 407, simethicone, carbomers, sodium benzoate, potassium sorbate, and disodium EDTA.

In a further aspect, the mucoadhesive polymer carrier is MucoLox™.

In a further aspect, the mucoadhesive polymer carrier is present in amount of from about 80 wt % to about 99 wt %. In a still further aspect, the mucoadhesive polymer carrier is present in amount of from about 85 wt % to about 99 wt %. In yet a further aspect, the mucoadhesive polymer carrier is present in amount of from about 90 wt % to about 99 wt %. In an even further aspect, the mucoadhesive polymer carrier is present in amount of from about 92 wt % to about 99 wt %. In a still further aspect, the mucoadhesive polymer carrier is present in amount of from about 95 wt % to about 99 wt %. In yet a further aspect, the mucoadhesive polymer carrier is present in amount of from about 97 wt % to about 99 wt %.

In a further aspect, the mucoadhesive polymer carrier is present in amount of from about 80 wt % to about 97 wt %. In an even further aspect, the mucoadhesive polymer carrier is present in amount of from about 80 wt % to about 95 wt %. In a still further aspect, the mucoadhesive polymer carrier is present in amount of from about 80 wt % to about 92 wt %.

In a further aspect, the mucoadhesive polymer carrier is present in amount of from about 91 wt % to about 98 wt %. In a still further aspect, the mucoadhesive polymer carrier is present in amount of from about 92 wt % to about 97 wt %. In yet a further aspect, the mucoadhesive polymer carrier is present in amount of from about 93 wt % to about 96 wt %. In an even further aspect, the mucoadhesive polymer carrier is present in amount of from about 94 wt % to about 95 wt %.

In a further aspect, the polysaccharide polymers are selected from pullulan, sodium hyaluronate, tamarind xyloglucan, and amylopectin. In a still further aspect, the polysaccharide polymers are selected from pullulan, sodium hyaluronate, and tamarind xyloglucan.

a. Amylopectin

Amylopectin is a water soluble polysaccharide and highly branched polymer of glucose found in plants. It is one of the two components of starch. Amylopectin provides excellent bio-adhesiveness. Excipient compositions including this compound do not produce irritation while attached to mucous membranes. In some aspects, amylopectin is derived from any food starch, such as, for example *Zea Mays* starch and waxy potato starch.

b. Pullulan

Pullulan is a polysaccharide polymer consisting of maltotriose units, also known as α-1,4; α-1,6-glucan. Three glucose units in maltotriose are connected by an α-1,4-glycosidic bond, whereas consecutive maltotriose units are connected to each other by an α-1,6-glycosidic bond. Pullulan is produced from starch by the fungus *Aureobasidium pullulans*. Pullulan is often used for glazing, as a film forming agent, and as coating, among others. Pullulan generates a transparent, water-soluble, fat-resistant, antistatic film of low oxygen permeability. Pullulan also provides excellent bio-adhesiveness. Excipient compositions including pullulan produce a strong attachment to mucous membranes.

c. Sodium Hyaluronate or Hyaluronic Acid

Sodium hyaluronate or hyaluronic acid (HA) is a biodegradable, biocompatible, non-toxic, non-immunogenic, unique viscoelastic, and non-inflammatory linear polyanionic polysaccharide that consists of N-acetyl-d-glucosamine and beta-glucuronic acid. It has extensive cosmetic, medical, and pharmaceutical applications. It contains disaccharide units of d-glucuronic acid and N-acetyl-d-glucosamine with (1→4) inter-glycosidic linkage and also has good mucoadhesion property. It forms a gel with water and is found in every vertebrate and some bacteria. In addition to being used as a polymer for cancer targeting, HA is also used in ophthalmic, pulmonary, nasal, brain, and skin application (Liao et al. (2005) *Drug Deliv.* 12 (6): 327-342). HA is often included within excipient compositions as a lubricant and moisturizing agent.

d. Tamarind Xyloglucan

Xyloglucans are members of a group of polysaccharides typically referred to as hemicelluloses. Hemicelluloses are plant cell wall polysaccharides that are not solubilized by water; rather, they are solubilized by aqueous alkali salts. Xyloglucans of *Tamarindus indica*L. (Fabaceae) have been described as a viscosity enhancer showing mucomimetic, mucoadhesive, and bioadhesive activities. Therefore, excipient compositions include tamarind xyloglucan for systemic delivery of pharmaceutical agents as they prolong the residence time, and thus, reduce the washout of, the pharmaceutical agent.

2. Insulin

In one aspect, the disclosed composition comprises insulin. Insulin is a hormone produced by beta cells of the pancreas, and is considered to be the main anabolic hormone of the body. It regulates the metabolism of carbohydrates, fats, and protein by, inter alia, promoting the absorption of glucose from the blood into fat, liver, and skeletal muscle cells. Although insulin disturbance is associated with a variety of disorders including insulinoma, metabolic syndrome, and polycystic ovary syndrome, it is primarily associated with diabetes (e.g., type 1 diabetes and type 2 diabetes).

Several different types of insulin are available depending on how quickly they work, when they peak, and how long they last. Specifically, insulin can be rapid-acting (e.g., insulin glulisine, insulin lispro, and insulin aspart), regular or short-acting (e.g., Humulin R and Novolin R), intermediate-acting (e.g., Humulin N and Novloin N), or long-acting (e.g., insulin detemir and insulin glargine). Insulin may be administered as a mixture of the different types (i.e., pre-mixed; simultaneously). Alternatively, the different types of insulin can be administered separately (i.e., sequentially).

In a further aspect, the insulin is rapid-acting, short-acting, long-acting, or a combination thereof.

In a further aspect, the insulin is present in an amount of from about 1 wt % to about 20 wt %. In a still further aspect, the insulin is present in an amount of from about 1 wt % to about 15 wt %. In yet a further aspect, the insulin is present in an amount of from about 1 wt % to about 10 wt %. In an even further aspect, the insulin is present in an amount of from about 1 wt % to about 8 wt %. In a still further aspect, the insulin is present in an amount of from about 1 wt % to about 6 wt %. In yet a further aspect, the insulin is present in an amount of from about 1 wt % to about 4 wt %. In an even further aspect, the insulin is present in an amount of from about 1 wt % to about 2 wt %.

In a further aspect, the insulin is present in an amount of from about 2 wt % to about 10 wt %. In a still further aspect, the insulin is present in an amount of from about 4 wt % to about 10 wt %. In yet a further aspect, the insulin is present in an amount of from about 6 wt % to about 10 wt %. In an even further aspect, the insulin is present in an amount of from about 8 wt % to about 10 wt %.

In a further aspect, the insulin is present in an amount of from about 2 wt % to about 9 wt %. In a still further aspect, the insulin is present in an amount of from about 3 wt % to about 8 wt %. In yet a further aspect, the insulin is present in an amount of from about 4 wt % to about 7 wt %. In an even further aspect, the insulin is present in an amount of from about 5 wt % to about 6 wt %.

3. Optional Additives

In various aspects, the disclosed composition further comprises one or more additives. Thus, in one aspect, the disclosed composition further comprises one or more of an anti-infective agent, an anti-inflammatory agent, a neuropathic pain agent, and a vasodilating agent.

In a further aspect, the additive is present in an amount of from about 0.01 wt % to about 10 wt % of the composition. In a still further aspect, the additive is present in an amount of from about 0.01 wt % to about 8 wt % of the composition. In yet a further aspect, the additive is present in an amount of from about 0.01 wt % to about 6 wt % of the composition. In an even further aspect, the additive is present in an amount of from about 0.01 wt % to about 4 wt % of the composition. In a still further aspect, the additive is present in an amount of from about 0.01 wt % to about 2 wt % of the composition. In yet a further aspect, the additive is present in an amount of from about 0.01 wt % to about 1 wt % of the composition. In an even further aspect, the additive is present in an amount of from about 0.1 wt % to about 10 wt % of the composition. In a still further aspect, the additive is present in an amount of from about 1 wt % to about 10 wt % of the composition. In yet a further aspect, the additive is present in an amount of from about 2 wt % to about 10 wt % of the composition. In an even further aspect, the additive is present in an amount of from about 4 wt % to about 10 wt % of the composition. In a still further aspect, the additive is present in an amount of from about 6 wt % to about 10 wt % of the composition. In yet a further aspect, the additive is present in an amount of from about 8 wt % to about 10 wt % of the composition.

In a further aspect, the disclosed composition further comprises an anti-infective agent. Examples of anti-infective agents include, but are not limited to, amebicides (e.g., chloroquine phosphate, iodoquinol, metronidazole, paromomycin), aminoglycosides (e.g., neomycin, amikacin, gentamicin, kanamycin, streptomycin, tobramycin), anthelmintics (e.g., benzimidazoles, ivermectin, praziquantel, pyrantel), antifungal agents (e.g., terbinafine, anidulafungin, caspofungin, micafungin sodium, flucytosine, griseofulvin, ketoconazole, amphotericin B, nystatin, fluconazole, isavuconazonium sulfate, itraconazole, posaconazole, voriconazole), antiprotozoals (e.g., atovaquone, benznidazole, miltefosine, nitazoxanide, pentamidine isethionate, secnidazole, tinidazole), antiviral agents (e.g., acyclovir (acycloguanosine) (systemic), famciclovir, valacyclovir, cidofovir, entecavir, foscarnet sodium (phosphonoformic acid; PFA), ganciclovir (DHPG), hepatitis C virus direct-acting antivirals, letermovir, oseltamivir, peramivir, ribavirinrimantadine hydrochloride, telbivudine, valganciclovir, zanamivir, adefovir dipivoxil, amantadine hydrochloride), bacitracin, carbapenems (e.g., doripenem, ertapenem, imipenem-cilastatin, meropenem), cephalosporins (e.g., cefadroxil, cefazolin, cephalexin, cefprozil, cefuroxime, cefdinir, cefixime, cefotaxime, cefpodoxime, ceftazidime, ceftibuten, ceftriaxone, cefepime, ceftaroline), chloramphenicol, colistimethate sodium, fluoroquinolones (e.g., ciprofloxacin, gemifloxacin, levofloxacin, moxifloxacin, norfloxacin, ofloxacin), folate antagonists (e.g., trimethoprim), glycylcyclines (e.g., tigecycline), ketolides (e.g., telithromycin), leprostatics (e.g., dapsone), lincosamides (e.g., clindamycin, lincomycin), lipoglycopeptides (e.g., dalbavancin, oritavancin, telavancin), lipopeptides (e.g., daptomycin), macrolides (e.g., azithromycin, clarithromycin, erythromycin, fidaxomicin), methenamines, metronidazole, monobactams (e.g., aztreonam), nitrofurans (e.g., nitrofurantion), oxazolidinones (e.g., linezolid, tedizolid phosphate), penicillins (e.g., penicillin G, penicillin V, dicloxacillin, nafcillin, oxacillin, amoxicillin, amoxicillin/potassium clavulanate, ampicillin, ampicillin/sulbactam, piperacillin/tazobactam sodium, ticarcillin/potassium clavulanate), polymyxin B sulfate, rifaximin, streptogramins (e.g., quinupristin/dalfopristin), sulfadiazine, tetracyclines (e.g., demeclocycline, doxycycline, minocycline, tetracycline), and vancomycin.

In a further aspect, the disclosed composition further comprises an anti-inflammatory agent. Examples of anti-inflammatory agents include, but are not limited to, glucocorticoids (e.g., betamethasone, budesonide, cortisone, defalzacort, dexamethasone, hydrocortisone, methylprednisolone, prednisolone, prednisone, triamcinolone), NSAIDs (e.g., acetic acids such as diclofenax, indomethacin, sulindac, and tolmetin; COX-2 inhibitors such as celecoxib; fenamates such as meclofenamate and mefenamic acid; naphthylalkanones such as nabumetone; oxicams such as piroxicam and meloxicam; propionic acids such as fenoprofen, flurbiprofen, ibuprofen, ketoprofen, naproxen, and oxaprozin; pyranocarboxylic acids such as etodolac; pyrrolizine carboxylic acids such as ketorolac), and salicylates (e.g., aspirin, choline magnesium trisalicylate, diflunisal, magnesium salicylate, salsalate).

In a further aspect, the disclosed composition further comprises a neuropathic pain agent. Examples of neuropathic agents include, but are not limited to, tricyclic antidepressants (e.g., amitriptyline), anticonvulsants (e.g., gabapentin), local anesthetics (e.g., lidocaine), corticosteroids, and capsaicin cream.

In a further aspect, the disclosed composition further comprises a vasodilating agent. Examples of vasodilating agents include, but are not limited to, alprostadil, amyl nitrite, dipyridamole, epoprostenol, isosorbide dinitrate, isosorbide mononitrate, nimodipine, nitroglycerin, papaverine, and tolazoline.

C. Methods of Making a Composition

In one aspect, disclosed are methods for making a disclosed topical composition, the method comprising the step of combining insulin and a pharmaceutically acceptable topical carrier, wherein the carrier is not a cyanoacrylate polymer carrier.

In a further aspect, the pharmaceutically acceptable topical carrier is a mucoadhesive polymer carrier. In a still further aspect, the mucoadhesive polymer carrier comprises at least two polysaccharide polymers.

In a further aspect, the mucoadhesive polymer carrier comprises pullulan, sodium hyaluronate, tamarind xyloglucan, and *Zea mays* starch.

In a further aspect, the polysaccharide polymers are selected from pullulan, sodium hyaluronate, tamarind xyloglucan, and amylopectin. In a still further aspect, the polysaccharide polymers are selected from pullulan, sodium hyaluronate, and tamarind xyloglucan.

In a further aspect, the mucoadhesive polymer carrier is present in amount of from about 80 wt % to about 99 wt %. In a still further aspect, the mucoadhesive polymer carrier is present in amount of from about 85 wt % to about 99 wt %. In yet a further aspect, the mucoadhesive polymer carrier is present in amount of from about 90 wt % to about 99 wt %. In an even further aspect, the mucoadhesive polymer carrier is present in amount of from about 92 wt % to about 99 wt %. In a still further aspect, the mucoadhesive polymer carrier is present in amount of from about 95 wt % to about 99 wt %. In yet a further aspect, the mucoadhesive polymer carrier is present in amount of from about 97 wt % to about 99 wt %.

In a further aspect, the mucoadhesive polymer carrier is present in amount of from about 80 wt % to about 97 wt %. In an even further aspect, the mucoadhesive polymer carrier is present in amount of from about 80 wt % to about 95 wt %. In a still further aspect, the mucoadhesive polymer carrier is present in amount of from about 80 wt % to about 92 wt %.

In a further aspect, the mucoadhesive polymer carrier is present in amount of from about 91 wt % to about 98 wt %. In a still further aspect, the mucoadhesive polymer carrier is present in amount of from about 92 wt % to about 97 wt %. In yet a further aspect, the mucoadhesive polymer carrier is present in amount of from about 93 wt % to about 96 wt %. In an even further aspect, the mucoadhesive polymer carrier is present in amount of from about 94 wt % to about 95 wt %.

In a further aspect, the insulin is rapid-acting, short-acting, long-acting, or a combination thereof.

In a further aspect, the insulin is present in an amount of from about 1 wt % to about 20 wt %. In a still further aspect, the insulin is present in an amount of from about 1 wt % to about 15 wt %. In yet a further aspect, the insulin is present in an amount of from about 1 wt % to about 10 wt %. In an even further aspect, the insulin is present in an amount of from about 1 wt % to about 8 wt %. In a still further aspect, the insulin is present in an amount of from about 1 wt % to about 6 wt %. In yet a further aspect, the insulin is present in an amount of from about 1 wt % to about 4 wt %. In an even further aspect, the insulin is present in an amount of from about 1 wt % to about 2 wt %.

In a further aspect, the insulin is present in an amount of from about 2 wt % to about 10 wt %. In a still further aspect, the insulin is present in an amount of from about 4 wt % to about 10 wt %. In yet a further aspect, the insulin is present in an amount of from about 6 wt % to about 10 wt %. In an even further aspect, the insulin is present in an amount of from about 8 wt % to about 10 wt %.

In a further aspect, the insulin is present in an amount of from about 2 wt % to about 9 wt %. In a still further aspect, the insulin is present in an amount of from about 3 wt % to about 8 wt %. In yet a further aspect, the insulin is present in an amount of from about 4 wt % to about 7 wt %. In an even further aspect, the insulin is present in an amount of from about 5 wt % to about 6 wt %.

D. Methods of Using the Compositions

The disclosed topical compositions of the invention are useful in treating or controlling skin ailments such as, for example, burns, sores, lacerations, blisters, insect bites, surgical incisions, and ulcers.

Wound healing is typically divided into three phases: (1) the inflammatory phase (immediate to 2-5 days); (2) the proliferative phase (2 days to 3 weeks); and (3) the remodeling/maturation phase (3 weeks to 2 years). During the inflammatory phase, blood vessels constrict at the injury site and platelets coalesce to prevent bleeding. Platelets attach to exposed collagen surface and other platelets via adhesive glycoproteins: fibrinogen, fibronectin, thrombospondin, and von Willebrand factor. Platelets release factors that attract other important cells to an injury site. Neutrophils enter the wound to fight infection and attract macrophages. Macrophages, in turn, break down necrotic debris and activate a fibroblast response, which is vital for wound healing. Fibroblasts are involved in the extracellular matrix (ECM) deposition and wound contraction vital for wound healing.

Elevated levels of glucose have been shown to impair wound healing. Specifically, in wound healing with high glucose levels, the cell walls become stiff and rigid, which impairs blood flow through the small vessels located in the surface of the wound. This wall impedes the flow and permeability of red blood cells that are required for the development of dermal tissue. Therefore, without wishing to be bound by theory, decreasing local site blood sugar can enhance oxygenation of the injured site and thereby increase tissue recovery. Moreover, with respect to diabetic ulcers specifically, diabetics are spilling glucose into the wound. Thus, the wound glucose level is markedly elevated over the systemic glucose level.

As shown in FIG. 1, during inflammatory phase diabetic wound healing, neutrophils migrate to the wound. The diabetic neutrophils overproduce peptidylargnine deiminase 4 (PAD4) and neutrophil extracellular traps (NET5), which, in turn, delays wound healing. Thus, reduction of PAD4 and/or NET5 should lead to wound healing. Without wishing to be bound by theory, insulin decreases PAD4 and NET5 by impairing the migration of neutrophils to the wound. In addition, topical application of insulin decreases wound glucose.

To treat or control the disorder, the compositions are administered to a subject in need thereof, such as a mammal, e.g., a human. The subject can be a human, non-human primate, horse, pig, rabbit, dog, sheep, goat, cow, cat, guinea pig, or rodent. The term does not denote a particular age or sex. Thus, adult and newborn subjects, whether male or female, are intended to be covered. The subject is preferably a mammal, such as a human. Prior to administering the compositions, the subject can be diagnosed with a need for treatment of a skin ailment, such as a burn, a sore, a laceration, a blister, an insect bite, a surgical incision, and an ulcer.

The compounds or compositions can be administered to the subject via topical administration. Administration can be continuous or intermittent. A preparation can be administered therapeutically; that is, administered to treat an existing disease or condition. A preparation can also be administered prophylactically; that is, administered for prevention of a skin ailment, such as a burn, a sore, a laceration, a blister, an insect bite, a surgical incision, and an ulcer.

The therapeutically effective amount or dosage of the composition can vary within wide limits. Such a dosage is adjusted to the individual requirements in each particular case including the specific composition(s) being administered and the condition being treated, as well as the patient being treated. In general, Single dose compositions can contain such amounts or submultiples thereof of the composition to make up the daily dose. The dosage can be adjusted by the individual physician in the event of any contraindications. Dosage can vary, and can be administered in one or more dose administrations daily, for one or several days.

In a further aspect, the subject is a mammal. In a still further aspect, the mammal is a human.

In a further aspect, the skin ailment is selected from a burn, a sore, a laceration, a blister, an insect bite, a surgical incision, and an ulcer. In a still further aspect, the skin ailment is a diabetic ulcer.

1. Treatment Methods

The compounds disclosed herein are useful for treating or controlling disorders associated with a skin ailment, in particular, a diabetic ulcer. Thus, provided is a method comprising administering a therapeutically effective amount of a disclosed composition to a subject. In a further aspect, the method can be a method for treating a skin ailment.

a. Treating a Skin Ailment

In one aspect, disclosed are methods for treating a skin ailment in a subject, the method comprising the step of topically administering to the skin ailment an effective amount of a disclosed topical composition. Examples of skin ailments include, but are not limited to, burns, sores, lacerations, blisters, insect bites, surgical incisions, and ulcers. In a further aspect, the skin ailment is an ulcer. In a still further aspect, the skin ailment is a diabetic ulcer.

In one aspect, disclosed are methods for treating a skin ailment having an outer edge in a subject, the method comprising the steps of: (a) obtaining a biological sample from the skin ailment or from a surrounding tissue, wherein the surrounding tissue is within about one inch of the outer edge; (b) measuring the subject's blood sugar levels in the biological sample; and (c) managing the wound via administration of an antibiotic, debridement, off-loading, revascularization, hyperbaric oxygen therapy, administration of a wound care product, negative-pressure wound therapy, or a combination thereof.

In one aspect, disclosed are methods for treating a skin ailment having an outer edge in a subject, the method comprising managing the wound via administration of an antibiotic, debridement, off-loading, revascularization, hyperbaric oxygen therapy, administration of a wound care product, negative-pressure wound therapy, or a combination thereof, wherein the subject was previously identified as being in need of treatment of the skin ailment by the steps of: (a) obtaining a biological sample from the skin ailment or from a surrounding tissue, wherein the surrounding tissue is within about one inch of the outer edge; and (b) measuring the subject's blood sugar levels in the biological sample.

Thus, for example, a skin ailment could be treated using a disclosed composition as follows:
1. Clean the skin ailment with soap and warm water, with either a wash cloth or gauze sponge. Cleaning may be lightly abrasive as the subject tolerates. Alternatively, the skin ailment can be cleaned with gauze, moistened with saline and hibiclens. Again, the cleaning may be lightly abrasive as the subject tolerates.
2. Rinse the ailment thoroughly with warm water or saline so no soap residue remains.
3. Apply the topical composition to a Q-Tip applicator and lightly cover the surface of the ailment with the composition. Do not glop on the ailment. If eschar is present, apply the composition to the edge of the eschar and beneath the edge of the eschar. The composition need not be applied to the top of the eschar.
4. Cover the ailment with dry gauze. Wrap and secure the gauze with Kling, Kerlex roll, or Ace wrap. The wrap should be loosely applied so as to secure the dressing but to not apply pressure to the ailment site.
5. If there is surrounding dermatitis (redness), allow the area to dry (no wrap need be applied).

In a further aspect, the subject has been diagnosed with a need for treatment of the skin ailment prior to the administering step. In a further aspect, the method further comprises the step of identifying a subject in need of treatment of the skin ailment. In a still further aspect, the skin ailment is a diabetic ulcer.

In a further aspect, the subject has been diagnosed with a need for treatment of diabetes prior to the administering step. In a further aspect, the method further comprises the step of identifying a subject in need of treatment of diabetes.

In a further aspect, the subject is a mammal. In a still further aspect, the mammal is a human.

In a further aspect, the effective amount is an amount effective to decrease blood sugar levels of the subject. In a still further aspect, the effective amount is an amount effective to decrease blood sugar levels of the subject by at least about 5%. In yet a further aspect, the effective amount is an amount effective to decrease blood sugar levels of the subject by at least about 10%. In an even further aspect, the effective amount is an amount effective to decrease blood sugar levels of the subject by at least about 15%. In a still further aspect, the effective amount is an amount effective to decrease blood sugar levels of the subject by at least about 25%. In yet a further aspect, the effective amount is an amount effective to decrease blood sugar levels of the subject by at least about 50%. In an even further aspect, the effective amount is an amount effective to decrease blood sugar levels of the subject by at least about 75%. In a still further aspect, the effective amount is an amount effective to decrease blood sugar levels of the subject by at least about 80%.

In a further aspect, obtaining a biological sample is via a lancing device, a syringe, or via scraping the skin ailment. Examples of biological samples include, but are not limited to, blood, serum, and plasma. In a further aspect, the biological sample is blood.

In a further aspect, the subject's blood sugar level is greater than the subject's blood sugar level measured in a biological sample obtained from the subject's finger.

In a further aspect, the biological sample is obtained from the skin ailment. In a still further aspect, the biological sample is obtained from the surrounding tissue.

In a further aspect, the surrounding tissue is within about three-fourth inch of the outer edge. In a still further aspect, the surrounding tissue is within about one-half inch of the outer edge. In yet a further aspect, the surrounding tissue is within about one-fourth inch of the outer edge.

In a further aspect, the subject's blood sugar level is greater than about 180 mg/dl. In a still further aspect, the subject's blood sugar level is greater than about 200 mg/dl. In yet a further aspect, the subject's blood sugar level is greater than about 250 mg/dl. In an even further aspect, the subject's blood sugar level is greater than about 300 mg/dl. In a still further aspect, the subject's blood sugar level is greater than about 350 mg/dl. In yet a further aspect, the subject's blood sugar level is greater than about 400 mg/dl. In an even further aspect, the subject's blood sugar level is greater than about 450 mg/dl. In a still further aspect, the subject's blood sugar level is greater than about 500 mg/dl. In yet a further aspect, the subject's blood sugar level is greater than about 550 mg/dl. In an even further aspect, the subject's blood sugar level is greater than about 600 mg/dl.

In a further aspect, managing the wound is via administration of an antibiotic, debridement, off-loading, revascularization, hyperbaric oxygen therapy, administration of a wound care product, negative-pressure wound therapy, advanced moist wound therapy, or a combination thereof.

In a further aspect, managing the wound is via administration of an antibiotic. Examples of antibiotics include, but are not limited to, lipopeptides, fluoroquinolone, lipoglycopeptides, macrolides, β-lactams such as penicillins, cephalosporins, monobactams, and carbapenems, lincosamides, streptogramins, aminoglycosides, quinolones, sulfonamides, tetracyclines, chloramphenicol, metronidazole, tinidazole, nitrofurantoin, glycopeptides, lipoglycopeptides, oxazolidinones, rifamycins, polypeptides, and tuberactinomycins.

In a further aspect, managing the wound is via debridement. Examples of types of debridement include, but are not limited to, autolytic, enzymatic, surgical, mechanical, and via maggots.

In a further aspect, managing the wound is via off-loading.

In a further aspect, managing the wound is via revascularization.

In a further aspect, managing the wound is via hyperbaric oxygen therapy.

In a further aspect, managing the wound is via administration of a wound care product. Examples of wound care products include, but are not limited to, debriding agents, polyurethane foams, hydrogels, transparent films, hydrocolloids, hydro-fibers, alginates, dressings, collagen, lidocaine, and platelet-derived growth factors. In yet a further aspect, the wound car product comprises a topical composition comprising insulin and a pharmaceutically acceptable topical carrier. In an even further aspect, the pharmaceutically acceptable topical carrier is a mucoadhesive polymer. In a still further aspect, the mucoadhesive polymer carrier comprises at least two polysaccharide polymers. In yet a further aspect, the carrier is not a cyanoacrylate polymer carrier.

In a still further aspect, the wound care product comprises a topical composition comprising: (a) a mucoadhesive polymer carrier comprising at least two polysaccharide polymers; and (b) insulin.

In a further aspect, managing the wound is via advanced moist wound therapy.

In a further aspect, the method further comprises administering to the subject at least one agent selected from an anti-infective agent, an anti-inflammatory agent, a neuropathic pain agent, and a vasodilating agent. In a still further aspect, the composition and the agent are administered sequentially. In yet a further aspect, the composition and the agent are administered simultaneously.

2. Methods of Modifying PAD4 and/or NETs Activity in a Subject

In one aspect, disclosed are methods of modifying peptidylarginine deimnase (PAD4) and/or neutrophil extracellular traps (NETs) activity in a subject having a skin ailment, the method comprising the step of topically administering to the skin ailment an effective amount of a disclosed topical composition.

In diabetes, neutrophils are activated to over produce peptidylarginine deimnase (PAD4) and neutrophil extracellular traps (NETs), which are key factors in delayed wound healing. Specifically, neutrophil elastase, a component of NETS, can lead to degradation of the wound matrix. Thus, without wishing to be bound by theory, inhibition of PAD4 and NETs should be a viable approach to wound healing.

Insulin is a peptide hormone made of 51 amino acids and having a molecular weight of 5808DA. It is naturally produced in the islets of Langerhans in the pancreas. Additionally, insulin is synthetically produced and is used by millions worldwide for the management of diabetes. Although insulin is primarily known for its role in glucose control, it also has other effects. For example, insulin negatively regulates the acute inflammatory response by impairing neutrophil function, concomitantly enhances the phagocytic activity of macrophages and the production of $H_2O_2$ by macrophages, and increases the metabolism of glucose. In addition, insulin impairs neutrophil migration to the wound, which in turn leads to a decrease in NETs and PAD4. Studies have also shown that a lack of NETs does not worsen bacteremia (infection) in PAD4 deficient animals. This is presumed to be secondary to insulin causing enhanced phagocytic capacity of macrophages and increased production of $H_2O_2$, which helps eliminate microbial contamination. Studies have shown that the net inhibition that will enhance wound healing in diabetics does not cause a host to be vulnerable to bacterial infection.

One additional role of insulin is to increase the metabolism of glucose and to decrease that of glutaminase. Glutaminase catalyzes the following reaction:

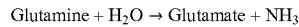

$$\text{Glutamine} + H_2O \rightarrow \text{Glutamate} + NH_3$$

In oxonal terminals of neurons of the CNS, glutamate is the most abundantly used excitatory neurotransmitter. After release into the synapse for neurotransmission, glutamate is rapidly taken by astrocytes and converted to glutamine. The glutamine is supplied to presynaption terminals of neurons where glutaminase converts back to glutamate for loading into synaptic vesicles.

Herein, topical application of insulin directly in the wound decreases the wound glucose level, which significantly enhances healing.

In a further aspect, modifying is inhibiting. In a further aspect, modifying is decreasing.

In a further aspect, the subject is a mammal. In a still further aspect, the subject is a human.

In a further aspect, the subject has been diagnosed with a need for treatment of a skin ailment prior to the administering step. In a still further aspect, the method further comprises the step of identifying a subject in need of treatment of a skin ailment. In yet a further aspect, the skin ailment is a diabetic ulcer.

In a further aspect, the subject has been diagnosed with a need for treatment of diabetes prior to the administering step.

In a further aspect, the subject has been diagnosed with a need for treatment of a disorder associated with PAD4 and/or NETs activity dysfunction prior to the administering step. In a still further aspect, the method further comprises the step of identifying a subject in need of treatment of a disorder associated with PAD4 and/or NETs activity dysfunction. In yet a further aspect, the disorder associated with PAD4 and/or NETs activity dysfunction is diabetes.

In a further aspect, the subject has been diagnosed with a need for modifying PAD4 and/or NETs activity prior to the administering step. In a still further aspect, the subject has been diagnosed with a need for inhibiting PAD4 and/or NETs activity prior to the administering step.

3. Methods of Modifying PAD4 and/or NETs Activity in at Least One Cell

In one aspect, disclosed are methods of modifying peptidylarginine deimnase (PAD4) and/or neutrophil extracellular traps (NETs) activity in a skin ailment having at least one cell, the method comprising topically contacting at least one cell with an effective amount of a disclosed topical composition.

In a further aspect, modifying is inhibiting. In a still further aspect, modifying is decreasing.

In a further aspect, the cell is mammalian. In a still further aspect, the cell is human. In yet a further aspect, the cell has been isolated from a mammal prior to the contacting step.

In a further aspect, contacting is via administration to a subject. In a still further aspect, contacting is via topical administration to a subject.

In a further aspect, the subject has been diagnosed with a need for modification of PAD4 and/or NETs activity prior to the administering step. In a still further aspect, the subject has been diagnosed with a need for treatment of a disorder associated with PAD4 and/or NETs activity dysfunction.

4. Use of Compounds

In one aspect, the invention relates to the use of a disclosed composition or a product of a disclosed method. In a further aspect, a use relates to the manufacture of a medicament for the treatment of a skin ailment in a subject.

Also provided are the uses of the disclosed compositions and products. In one aspect, the invention relates to use of at least one disclosed composition. In a further aspect, the composition used is a product of a disclosed method of making.

In a further aspect, the use relates to a process for preparing a pharmaceutical composition comprising a therapeutically effective amount of a disclosed composition or a product of a disclosed method of making, for use as a medicament.

In a further aspect, the use relates to a process for preparing a pharmaceutical composition comprising a therapeutically effective amount of a disclosed composition or a product of a disclosed method of making, wherein a pharmaceutically acceptable carrier is intimately mixed with a therapeutically effective amount of the composition or the product of a disclosed method of making.

In various aspects, the use relates to a treatment of a skin ailment in a subject. In one aspect, the use is characterized in that the subject is a human. In one aspect, the use is characterized in that the skin ailment is a diabetic ulcer.

In a further aspect, the use relates to the manufacture of a medicament for the treatment of a skin ailment in a subject.

It is understood that the disclosed uses can be employed in connection with the disclosed compositions, products of disclosed methods of making, methods, and kits. In a further aspect, the invention relates to the use of a disclosed composition or a disclosed product in the manufacture of a medicament for the treatment of a skin ailment in a mammal. In a further aspect, the skin ailment is a diabetic ulcer.

5. Manufacture of a Medicament

In one aspect, the invention relates to a method for the manufacture of a medicament for treating a skin ailment in a subject having the skin ailment, the method comprising combining a therapeutically effective amount of a disclosed composition or product of a disclosed method with a pharmaceutically acceptable carrier or diluent.

As regards these applications, the present method includes the administration to an animal, particularly a mammal, and more particularly a human, of a therapeutically effective amount of the composition effective in the treatment of a skin ailment. The dose administered to an animal, particularly a human, in the context of the present invention should be sufficient to affect a therapeutic response in the animal over a reasonable time frame. One skilled in the art will recognize that dosage will depend upon a variety of factors including the condition of the animal and the body weight of the animal.

The size of the dose also will be determined by the route, timing, and frequency of administration as well as the existence, nature, and extent of any adverse side effects that might accompany the administration of the composition and the desired physiological effect. It will be appreciated by one of skill in the art that various conditions or disease states, in particular chronic conditions or disease states, may require prolonged treatment involving multiple administrations.

Thus, in one aspect, the invention relates to the manufacture of a medicament comprising combining a disclosed composition or a product of a disclosed method of making, with a pharmaceutically acceptable carrier or diluent.

6. Kits

In one aspect, the invention relates to a kit comprising a disclosed topical composition and one or more of: (a) an agent known to treat a skin ailment; and (b) instructions for treating a skin ailment. Examples of skin ailments include, but are not limited to, burns, sores, lacerations, blisters, insect bites, surgical incisions, and ulcers. In a further aspect, the skin ailment is an ulcer. In a still further aspect, the skin ailment is a diabetic ulcer.

Examples of agents known to treat skin ailments include, but are not limited to, emollients, keratolytics, local anesthetic agents, local antipruritic agents, antibacterial agents, antiviral agents, antifungal agents, anti-inflammatory agents, antiparasiticidal agents, debriding agents, antineoplastic agents, burn treatment agents, eczema agents, psoriasis agents, and agents known for the treatment of diabetic foot ulcers.

In a further aspect, the at least one compound and the at least one agent are co-formulated. In a further aspect, the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

E. Examples

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The Examples are provided herein to illustrate the invention, and should not be construed as limiting the invention in any way. Examples are provided herein to illustrate the invention and should not be construed as limiting the invention in any way.

1. Preparation of Topical Compositions

A series of topical compositions were prepared containing different types of insulin present in an amount from 1 wt % to 10 wt % (see Table 1 below). Briefly, the compounding/dispensing area was cleaned with 70% isopropyl rubbing alcohol. Next, the insulin was removed from the box and the vial sprayed with 70% isopropyl rubbing alcohol under a Nuaire Powder containment hood, before being allowed to dry. The insulin was then withdrawn from the original container via a syringe and needle and added to a clean, appropriately sized electronic mortar & pestle (EMP) jar. Mucolox™ was added to the desired final weight. The composition was mixed using EMP on a low setting (2) for 45 seconds.

TABLE 1

| No. | Insulin Type | Insulin Concentration (units per gram) | Mucolox ™ Concentration (units per gram) |
|---|---|---|---|
| 1 | Humalog | 1 | 99 |
| 2 | Humalog | 2 | 98 |
| 3 | Humalog | 3 | 97 |
| 4 | Humalog | 4 | 96 |
| 5 | Humalog | 5 | 95 |
| 6 | Humalog | 6 | 94 |
| 7 | Humalog | 7 | 93 |
| 8 | Humalog | 8 | 92 |
| 9 | Humalog | 9 | 91 |
| 10 | Humalog | 10 | 90 |
| 11 | Humulin R | 1 | 99 |
| 12 | Humulin R | 2 | 98 |
| 13 | Humulin R | 3 | 97 |
| 14 | Humulin R | 4 | 96 |
| 15 | Humulin R | 5 | 95 |
| 16 | Humulin R | 6 | 94 |
| 17 | Humulin R | 7 | 93 |
| 18 | Humulin R | 8 | 92 |
| 19 | Humulin R | 9 | 91 |
| 20 | Humulin R | 10 | 90 |
| 21 | Lantus | 1 | 99 |
| 22 | Lantus | 2 | 98 |
| 23 | Lantus | 3 | 97 |
| 24 | Lantus | 4 | 96 |
| 25 | Lantus | 5 | 95 |
| 26 | Lantus | 6 | 94 |
| 27 | Lantus | 7 | 93 |
| 28 | Lantus | 8 | 92 |
| 29 | Lantus | 9 | 91 |
| 30 | Lantus | 10 | 90 |
| 31 | Levemir | 1 | 99 |
| 32 | Levemir | 2 | 98 |
| 33 | Levemir | 3 | 97 |
| 34 | Levemir | 4 | 96 |
| 35 | Levemir | 5 | 95 |
| 36 | Levemir | 6 | 94 |
| 37 | Levemir | 7 | 93 |
| 38 | Levemir | 8 | 92 |
| 39 | Levemir | 9 | 91 |
| 40 | Levemir | 10 | 90 |
| 41 | Novolin R | 1 | 99 |
| 42 | Novolin R | 2 | 98 |
| 43 | Novolin R | 3 | 97 |
| 44 | Novolin R | 4 | 96 |
| 45 | Novolin R | 5 | 95 |
| 46 | Novolin R | 6 | 94 |
| 47 | Novolin R | 7 | 93 |
| 48 | Novolin R | 8 | 92 |
| 49 | Novolin R | 9 | 91 |
| 50 | Novolin R | 10 | 90 |
| 51 | Novolog | 1 | 99 |
| 52 | Novolog | 2 | 98 |
| 53 | Novolog | 3 | 97 |
| 54 | Novolog | 4 | 96 |
| 55 | Novolog | 5 | 95 |
| 56 | Novolog | 6 | 94 |
| 57 | Novolog | 7 | 93 |
| 58 | Novolog | 8 | 92 |
| 59 | Novolog | 9 | 91 |
| 60 | Novolog | 10 | 90 |

2. Evaluation of Wound Site Treated with a Topical Composition Containing Zinc Oxide and Insulin The patient was a 57 year old, extremely obese female with poor circulation in her lower extremities. She had a wound on her left leg that had been there for over a year and would not heal. The leg itself appeared blue and the wound was deep with significant drainage. Doctors had previously recommended she have the leg amputated due to constant infection. Checking the patient's blood sugar levels via a finger stick indicated that her blood sugar was within a range where healing of a wound would be predicted to occur (i.e., from about 110 to about 170, preferably from about 110 to about 140); however, a stick directly at the wound site revealed drastically different blood sugar levels (i.e., over 600). The wound was measured and then a composition containing between 5 to 8 units of regular insulin and about a teaspoon of baby cream was applied to the wound. After application, gauze was placed over, and then wrapped around, the wound. The next day, the drainage visually appeared to be much less. As before, blood sugar levels checked via a finger stick appeared okay but blood sugar levels checked via a stick at the wound site were elevated, albeit less than the day before. On day 5 the wound had begun healing and scabbing over. An oxygen tube was applied to a makeshift bandage and placed on the wound, similar to a topical hyperbaric. The bandage remained in place for one hour. At this time, the compound was again applied to the wound. This process (i.e., the makeshift bandage with oxygen tube followed by application of the composition) was continued once daily. By week 4, the wound was completely closed and the tissue around the wound appeared pink and healthy. By week 6, the wound was a small scar.

3. Summary of Patient Wound Healing Study

Figure 2A:
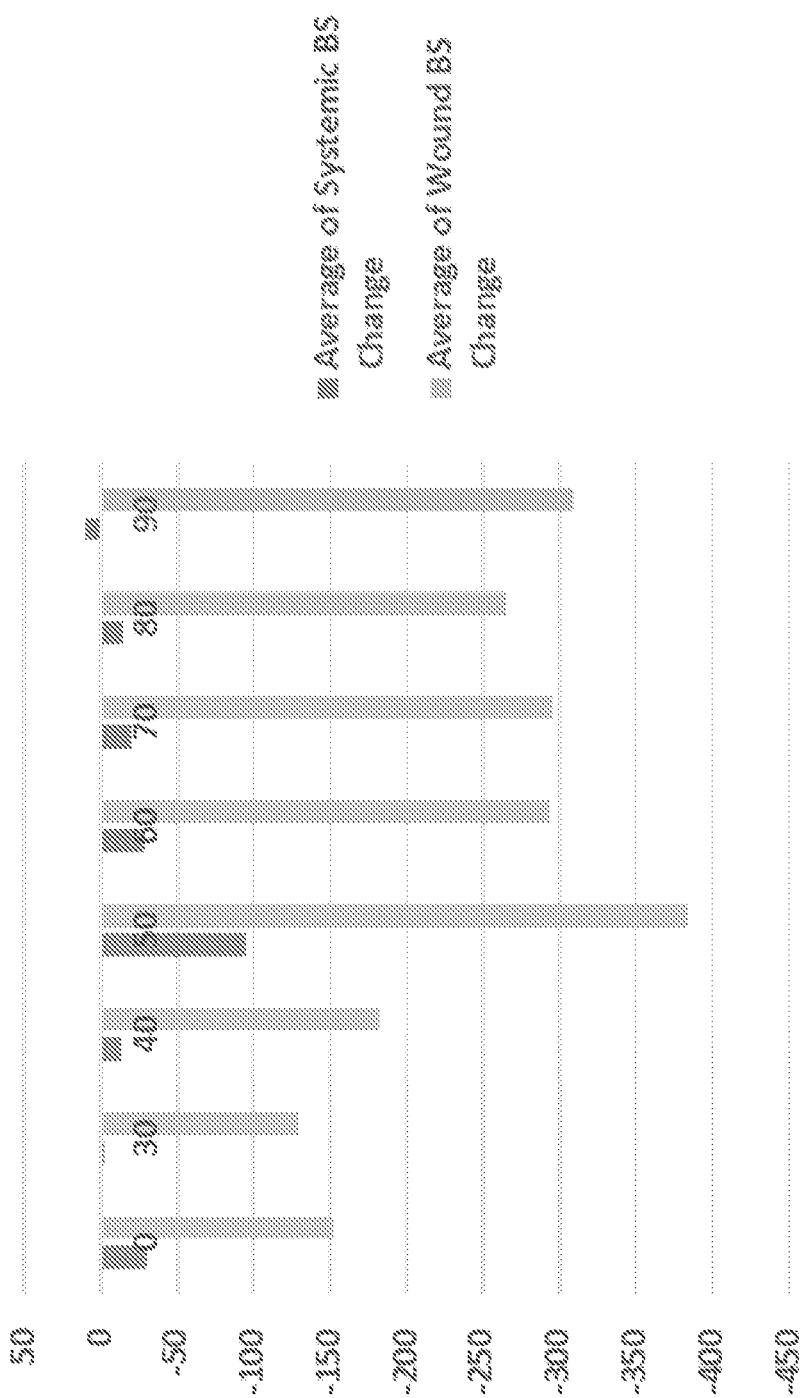
FIG. 2A and FIG. 2B show representative data illustrating the average blood sugar (BS) change by age (FIG. 2A) and class (FIG. 2B).
Figure 2B:
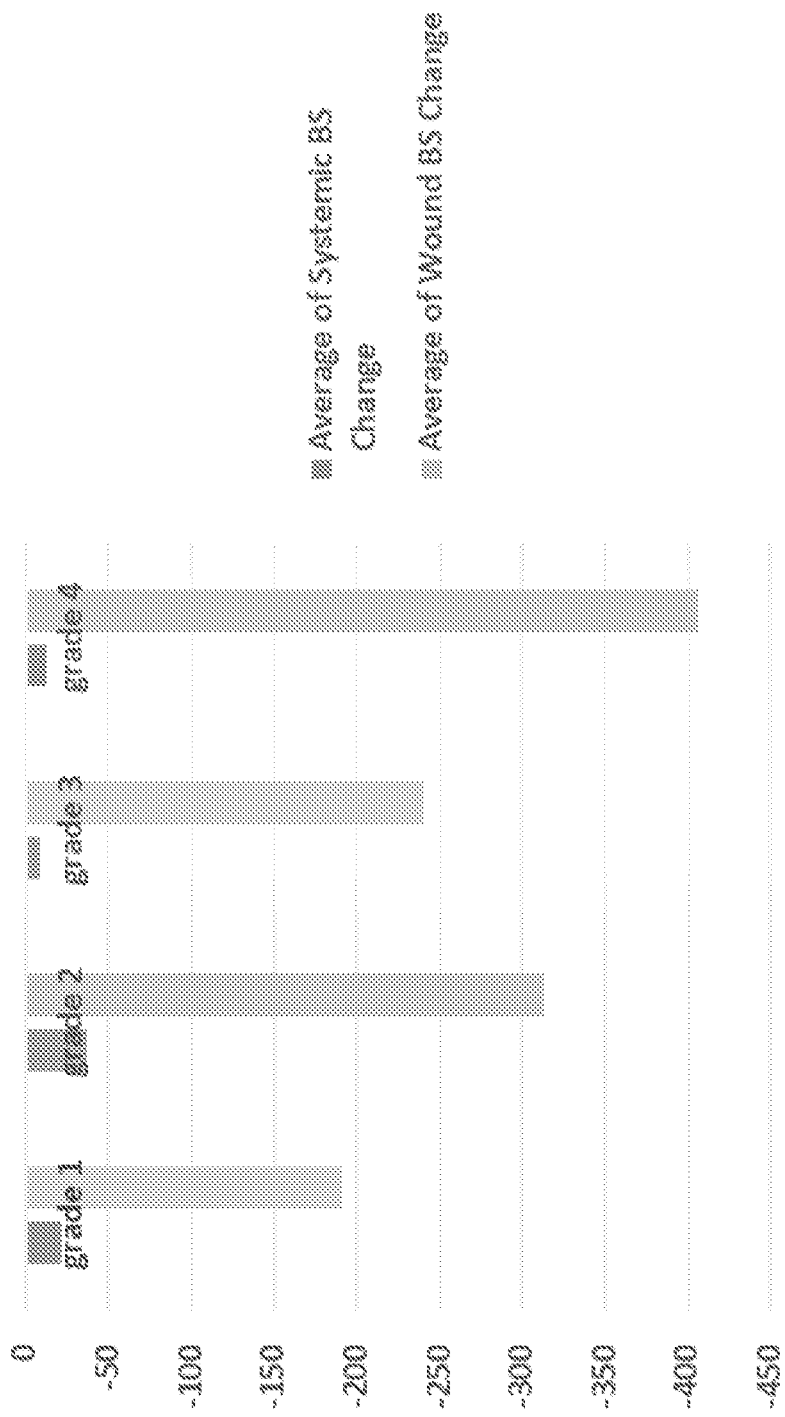
Figure 3A:
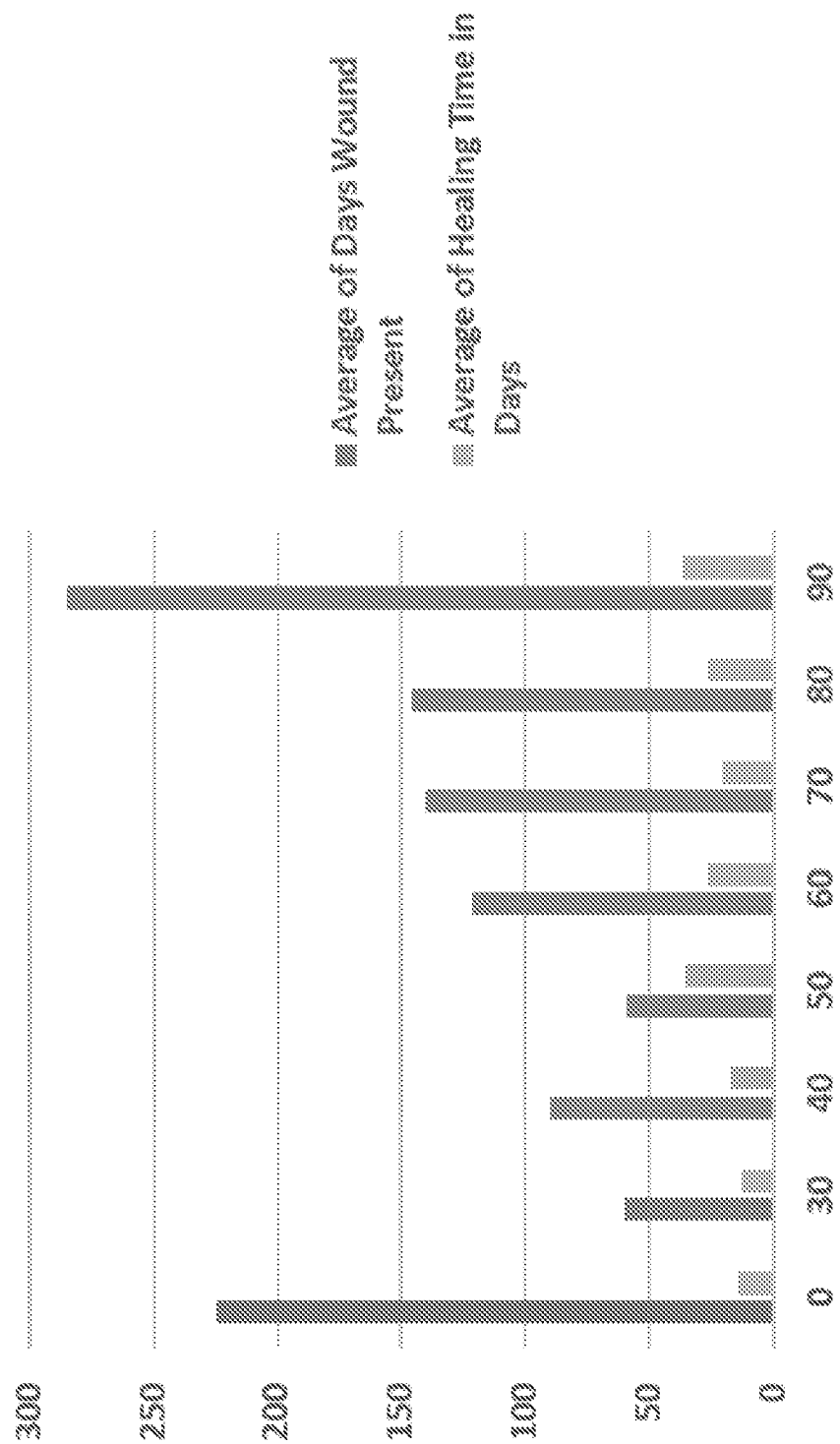
FIG. 3A and FIG. 3B show representative data illustrating the average heal time by age (FIG. 3A) and class (FIG. 3B).
Figure 3B:
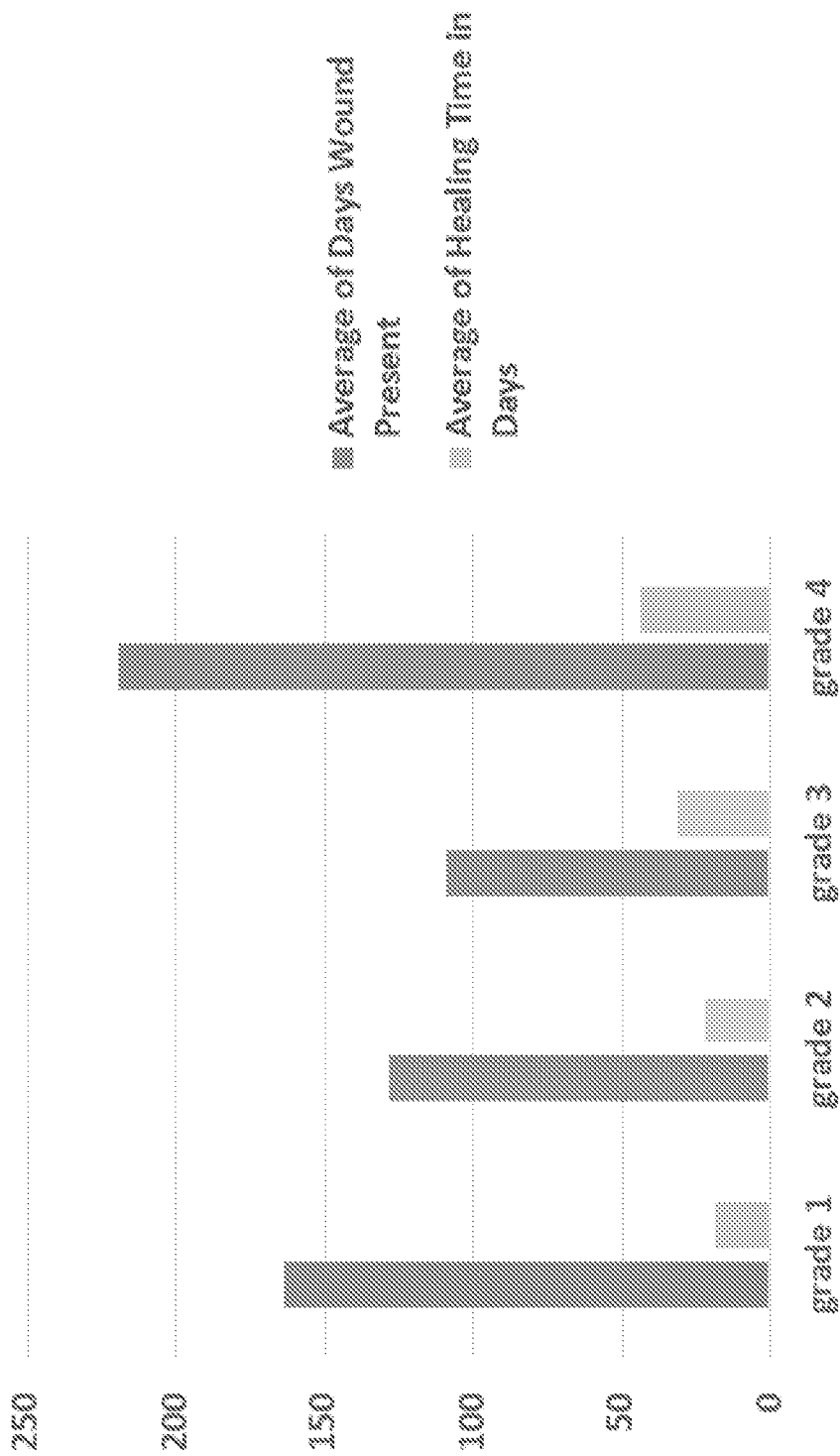

A summary of the results of a patient wound healing study are illustrated in Table 2 below. The average blood sugar (BS) change by age and class are shown in FIG. 2A and FIG. 2B, respectively. The average heal time by age and class are shown in FIG. 3A and FIG. 3B, respectively.

TABLE 2

| Patient No. | Age | Age Range | Wound Location | Wagener Class | Systemic BS | Wound BS |
|---|---|---|---|---|---|---|
| 1 | 71 | 70 | ankle 2.5 × 3 cm | grade 2 | 220 | 440 |
| 2 | 93 | 90 | rt 5th toe/rt ankle | grade 2 | 155 | 310 |
| 3 | 84 | 80 | lt heel 3 cm | grade 3 | 130 | 605 |
| 4 | 67 | 60 | Rt partial foot amp | grade 4 | 230 | 700 |
| 5 | 87 | 80 | rt great toe 1.5 cm | grade 3 | 160 | 208 |
| 6 | 56 | 50 | BKA ulcer 2.5 cm | grade 2 | 420 | 730 |
| 7 | | 0 | Facial dermatits | grade 1 | N/A | N/A |
| 8 | 70 | 70 | lt arm 5 cm × 5 cm | grade 2 | 150 | 305 |
| 9 | 71 | 70 | lt pre tibia 2.5 × 3 cm | grade 2 | 284 | 644 |
| 10 | 64 | 60 | surgical/toe amp | grade 4 | 101 | 384 |
| 11 | 63 | 60 | lt BKA 3 cm | grade 2 | 140 | 284 |
| 12 | 94 | 90 | rt foot | grade 4 | 140 | 600 |
| 13 | | 0 | lt foot | grade 1 | 126 | 422 |
| 14 | | 0 | rt foot | grade 1 | 260 | 290 |

TABLE 2-continued

| | | | | | | |
|---|---|---|---|---|---|---|
| 15 | 58 | 50 | lt groin/lt TMA | grade 3 | 165 | 387 |
| 16 | 44 | 40 | lt 4th toe | grade 1 | 188 | 387 |
| 17 | 77 | 70 | rt dorsum ft 4 cm | grade 2 | 204 | 490 |
| 18 | 67 | 60 | rt heel 1.3 cm | grade 1 | 278 | 500 |
| 19 | 88 | 80 | rt tibia | grade 1 | 175 | 280 |
| 20 | | 0 | lt arm | grade 1 | 190 | 305 |
| 21 | 83 | 80 | lt foot malper 3rd | grade 2 | 260 | 587 |
| 22 | 37 | 30 | lt ankle 2.3 cm | grade 1 | 110 | 275 |
| 23 | 84 | 80 | rt ankle | grade 1 | 148 | 475 |
| 24 | 72 | 70 | lt tibia | grade 1 | 137 | 344 |
| 25 | 61 | 60 | lt 5th toe | grade 2 | 187 | 463 |
| 26 | 86 | 80 | rt great toe | grade 2 | 190 | 535 |
| 27 | 81 | 80 | lt heel | grade 1 | 204 | 465 |

| Patient No. | Systemic BS at healing | Wound BS at healing | Systemic BS Change | Wound BS Change |
|---|---|---|---|---|
| 1 | 230 | 220 | 10 | −220 |
| 2 | 175 | 155 | 20 | −155 |
| 3 | 135 | 175 | 5 | −430 |
| 4 | 185 | 200 | −45 | −500 |
| 5 | 148 | 160 | −12 | −48 |
| 6 | 250 | 205 | −170 | −525 |
| 7 | | | | |
| 8 | | | | |
| 9 | 204 | 185 | −80 | −459 |
| 10 | 108 | 130 | 7 | −254 |
| 11 | 140 | 160 | 0 | −124 |
| 12 | 140 | 136 | 0 | −464 |
| 13 | 120 | 240 | −6 | −182 |
| 14 | 176 | 144 | −84 | −146 |
| 15 | 146 | 144 | −19 | −243 |
| 16 | 175 | 205 | −13 | −182 |
| 17 | 188 | 174 | −16 | −316 |
| 18 | 186 | 190 | −92 | −310 |
| 19 | 168 | 200 | −7 | −80 |
| 20 | 188 | 178 | −2 | −127 |
| 21 | 200 | 185 | −60 | −402 |
| 22 | 108 | 145 | −2 | −130 |
| 23 | 155 | 205 | 7 | −270 |
| 24 | 140 | 155 | 3 | −189 |
| 25 | 170 | 180 | −17 | −283 |
| 26 | 170 | 205 | −20 | −330 |
| 27 | 190 | 175 | −14 | −290 |

| Patient No. | Neuropathy | Neuropathy Resolved | ABI | Length time wound present | Days Wound Present | Time Until Healing |
|---|---|---|---|---|---|---|
| 1 | yes | yes | 0.47 | 6 mos | 180 | 15 days |
| 2 | no | N/A | 0.38 | 3 mos | 90 | 11 days |
| 3 | yes | yes | 0.36 | 8 mos | 240 | 21 days |
| 4 | yes | yes | 0.48 | 5 mos | 150 | 30 days |
| 5 | yes | yes | 0.9 | 2 mos | 60 | 20 days |
| 6 | no | N/A | 0.86 | 3 mos | 90 | 18 days |
| 7 | N/A | N/A | N/A | 18 mos | 540 | 10 days |
| 8 | N/A | N/a | N/A | 6 weeks | 42 | 16 days |
| 9 | N/A | N/A | 0.64 | 8 mos | 240 | 24 days |
| 10 | yes | yes | 0.47 | 4 weeks | 28 | 40 days |
| 11 | no | N/A | N/A | 11 days | 11 | 7 days |
| 12 | yes | yes | 0.34 | 16 mos | 480 | 62 days |
| 13 | yes | yes | 0.74 | 4 mos | 120 | 14 days |
| 14 | yes | yes | 1 | 6 mos | 180 | 15 days |
| 15 | yes | yes | 0.85 | 7 mos pre TMA/4 weeks PO | 28 | 53 days |
| 16 | no | N/A | 1 | 3 mos | 90 | 17 days |
| 17 | no | N/A | 0.75 | 5 mos | 150 | 31 days |
| 18 | no | N/A | 1 | 5 mos | 150 | 18 days |
| 19 | no | N/A | 0.8 | 4 mos | 120 | 11 days |
| 20 | no | N/A | 0.6 | 2 mos | 60 | 18 days |
| 21 | no | N/A | 0.42 | 4 mos | 120 | 38 days |
| 22 | no | N/A | 1 | 2 mos | 60 | 13 days |
| 23 | no | N/A | 0.78 | 6 mos | 180 | 27 days |
| 24 | yes | yes | 0.72 | 3 mos | 90 | 18 days |
| 25 | yes | yes | 0.56 | 9 mos | 270 | 37 days |
| 26 | no | N/A | 0.94 | 3 mos | 90 | 27 days |
| 27 | no | N/A | 0.56 | 7 mos | 210 | 43 days |

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating a diabetic foot ulcer in a human patient in need thereof, wherein the diabetic foot ulcer is refractory to systemic insulin the method comprising:
   (a) determining that the patient has a glucose level of greater than 200 mg/dL at the site of the diabetic foot ulcer that is greater than the patient's systemic blood glucose level; and
   (b) administering to the patient a pharmaceutical composition comprising insulin and a pharmaceutically acceptable carrier, wherein the pharmaceutical composition is topically administered to the patient at the site of the diabetic foot ulcer.

2. A method of treating a diabetic foot ulcer in a human patient in need thereof that has been determined to have a glucose level of greater than 200 mg/dL at the site of the diabetic foot ulcer that is greater than the patient's systemic blood glucose level wherein the diabetic foot ulcer is refractory to systemic insulin, the method comprising administering to the patient a pharmaceutical composition comprising insulin and a pharmaceutically acceptable carrier, wherein the pharmaceutical composition is topically administered to the patient at the site of the diabetic foot ulcer.

3. The method of claim 1, wherein the patient is determined to have a glucose level at the site of the diabetic foot ulcer of greater than 250 mg/dL.

4. The method of claim 3, wherein the patient is determined to have a glucose level at the site of the diabetic foot ulcer of greater than 300 mg/dL.

5. The method of claim 4, wherein the patient is determined to have a glucose level at the site of the diabetic foot ulcer of greater than 350 mg/dL.

6. The method of claim 5, wherein the patient is determined to have a glucose level at the site of the diabetic foot ulcer of greater than 400 mg/dL.

7. The method of claim 6, wherein the patient is determined to have a glucose level at the site of the diabetic foot ulcer of greater than 450 mg/dL.

8. The method of claim 7, wherein the patient is determined to have a glucose level at the site of the diabetic foot ulcer of greater than 500 mg/dL.

9. The method of claim 8, wherein the patient is determined to have a glucose level at the site of the diabetic foot ulcer of greater than 550 mg/dL.

10. The method of claim 9, wherein the patient is determined to have a glucose level at the site of the diabetic foot ulcer of greater than 600 mg/dL.

11. The method of claim 1, wherein the pharmaceutical composition is a gel, aerosol, cream, ointment, lotion, dusting powder, or jelly.

12. The method of claim 1, wherein the insulin is rapid-acting, short-acting, intermediate-acting, or long-acting.

13. The method of claim 12, wherein the rapid-acting insulin is insulin glulisine, insulin lispro, or insulin aspart.

14. The method of claim 12, wherein the long-acting insulin is insulin detemir or insulin glargine.

15. The method of claim 2, wherein the patient has been determined to have a glucose level at the site of the diabetic foot ulcer of greater than 250 mg/dL.

16. The method of claim 15, wherein the patient has been determined to have a glucose level at the site of the diabetic foot ulcer of greater than 300 mg/dL.

17. The method of claim 16, wherein the patient has been determined to have a glucose level at the site of the diabetic foot ulcer of greater than 350 mg/dL.

18. The method of claim 17, wherein the patient has been determined to have a glucose level at the site of the diabetic foot ulcer of greater than 400 mg/dL.

19. The method of claim 18, wherein the patient has been determined to have a glucose level at the site of the diabetic foot ulcer of greater than 450 mg/dL.

20. The method of claim 19, wherein the patient has been determined to have a glucose level at the site of the diabetic foot ulcer of greater than 500 mg/dL.

21. The method of claim 20, wherein the patient has been determined to have a glucose level at the site of the diabetic foot ulcer of greater than 550 mg/dL.

22. The method of claim 21, wherein the patient has been determined to have a glucose level at the site of the diabetic foot ulcer of greater than 600 mg/dL.

23. The method of claim 2, wherein the pharmaceutical composition is a gel, aerosol, cream, ointment, lotion, dusting powder, or jelly.

24. The method of claim 2, wherein the insulin is rapid-acting, short-acting, intermediate-acting, or long-acting.

25. The method of claim 24, wherein the rapid-acting insulin is insulin glulisine, insulin lispro, or insulin aspart.

26. The method of claim 24, wherein the long-acting insulin is insulin detemir or insulin glargine.

* * * * *